United States Patent
Andersson

Patent Number: 5,704,069
Date of Patent: Jan. 6, 1998

[54] COVER FOR SEALING RING OF AN EARMUFF

[75] Inventor: Lars-Gunnar Lennart Andersson, Höganäs, Sweden

[73] Assignee: Dalloz Safety AB, Billesholm, Sweden

[21] Appl. No.: 454,230

[22] PCT Filed: Feb. 9, 1994

[86] PCT No.: PCT/SE94/00103

§ 371 Date: Jun. 14, 1995

§ 102(e) Date: Jun. 14, 1995

[87] PCT Pub. No.: WO94/17764

PCT Pub. Date: Aug. 18, 1994

[30] Foreign Application Priority Data

Feb. 11, 1993 [SE] Sweden ............... 9300456-2

[51] Int. Cl.[6] .................................................. A61F 11/14
[52] U.S. Cl. ........................................ 2/209; 128/864
[58] Field of Search ............................... 2/209, 423, 455; 128/857, 864, 866, 867; 602/45; 604/378, 379

[56] References Cited

U.S. PATENT DOCUMENTS

| | | | |
|---|---|---|---|
| 2,622,159 | 12/1952 | Herman | 2/209 |
| 3,922,725 | 12/1975 | Csiki et al. | 2/209 |
| 4,438,163 | 3/1984 | Andersson | |
| 4,530,353 | 7/1985 | Lauritzen | 128/857 |
| 4,573,988 | 3/1986 | Pieniak et al. | 604/379 |

FOREIGN PATENT DOCUMENTS

| | | |
|---|---|---|
| 58 993/80 | 12/1981 | Australia . |
| 389604 | 11/1976 | Sweden . |
| 433907 | 6/1984 | Sweden . |

*Primary Examiner*—Diana Biefeld
*Attorney, Agent, or Firm*—Burns, Doane, Swecker & Mathis, L.L.P.

[57] ABSTRACT

Use of a superabsorbent nonwoven material in a moisture absorbing cover for an earmuff. A moisture absorbing ring-shaped cover for a sealing ring of an earmuff includes an inner layer (23) of super-absorbent fiber material. A device for use in moisture absorption at an earmuff comprises a cover (7) of this type and a supplementary cover (9) of the same construction intended for application within the earmuff and with a form corresponding to that of the area encompassed by the ring-shaped cover (7).

9 Claims, 2 Drawing Sheets

COVER FOR SEALING RING OF AN EARMUFF

The present invention relates to a moisture absorbing cover for an earmuff. The invention accordingly relates to a cover for a sealing ring of an earmuff, which sealing ring, after application of the earmuff over a person's ear, is intended to abut the person's head around the ear. The invention also relates to a device for use in moisture absorption in connection with an earmuff, which includes a cover of the above type and additionally a supplementary cover. Finally, the invention relates to use of a special material in a moisture absorbing cover for an earmuff.

Persons who protractedly wear earmuffs, such as hearing protecting muffs and/or communication headsets, are often troubled by sweat and moisture at the sealing rings and within the ear spaces of the earmuffs.

There have been attempts to resolve this problem by attaching exchangable layers of absorbent paper material to the sealing rings of earmuffs. In practice, however, this solution has not been found to give satisfactory results.

The object of the present invention is to provide an improved solution to the abovementioned moisture problems while using a moisture absorbing cover.

In accordance with the invention, this object is attained by a cover, a device and a use which bear the features indicated in the accompanying patent claims.

The invention is thus based on an insight that using a "superabsorbent" material in a moisture absorbing cover which is applied to an earmuff provides significant advantages. Over and above that such material has proven to provide extremely good moisture absorbance in this context, the material has proven to have the capacity to take up and retain moisture even under the present comparatively high pressure forces which are necessitated by the fact that the sealing ring of an earmuff must abut the person's head with a not insignificant force to obtain the desired sealing effect.

The superabsorbent material is preferably incorporated in an inner layer of the cover. With the aim of providing the wearer of the earmuff with a feeling of dryness and to ensure good moisture uptake, the cover should have an outer layer having a high moisture permeability or moisture transport effect so that the moisture is effectively conveyed thereby into the inner layer which contains the superabsorbent material.

The superabsorbent material is advantageously a fibrous material, preferably included in a nonwoven or bonded-fibre fabric layer. A layer of this sort, aside from the superabsorbent fibres, may include other fibres which provide stability and strength and which, in cooperation with similar fibres in optional enclosing other layers, may provide a cohesive and reinforcing elect. Such other fibres may be hydrophilic or wetting agent-treated fibres and/or staple fibres, "staple fibres" being used in a broad sense and not being limited, for example, to cut fibres.

The superabsorbent material is advantageously polyacrylate based.

Advantageously, the cover has an outer layer, an inner layer and a rear or backing layer, each of which is a nonwoven or bonded-fibre fabric layer. The preferred layer configurations and compositions, not least to provide good mechanical properties at a low cost, are apparent in the dependent patent claims.

In accordance with a further aspect of the invention, a cover of the sort under discussion may also be applied onto an earmuff at a location other than its sealing ring, namely within the ear space of the earmuff, whereby additionally improved moisture uptake is obtained. To this end, an extra, separate cover may be advantageously used, which is complementary to a ring-shaped cover intended for the sealing ring itself. The complementary cover, in other words, preferably has a configuration corresponding to the area which is encompassed by the ring-shaped cover, i.e. a configuration which also corresponds to the opening of the earmuff into the ear space.

A preferred embodiment of a device in accordance with the invention for use in moisture absorption in connection with an earmuff, comprises a first ring-shaped cover and a second cover complementary thereto, both covers being stamped out simultaneously, though separated from each other, from a flat web of material and releasably secured to a carrier by means of an adhesive attached to the rear side of the covers and intended for attachment onto the earmuff.

It will be appreciated that such devices can be simply manufactured and handled before application onto an earmuff, either individually or placed in an appropriate number on a suitable carrier, for example in the form of a sheet or a continuous band.

The invention will now be described in greater detail in relation to an exemplary embodiment and with reference the accompanying drawings, in which.

Figure 1:
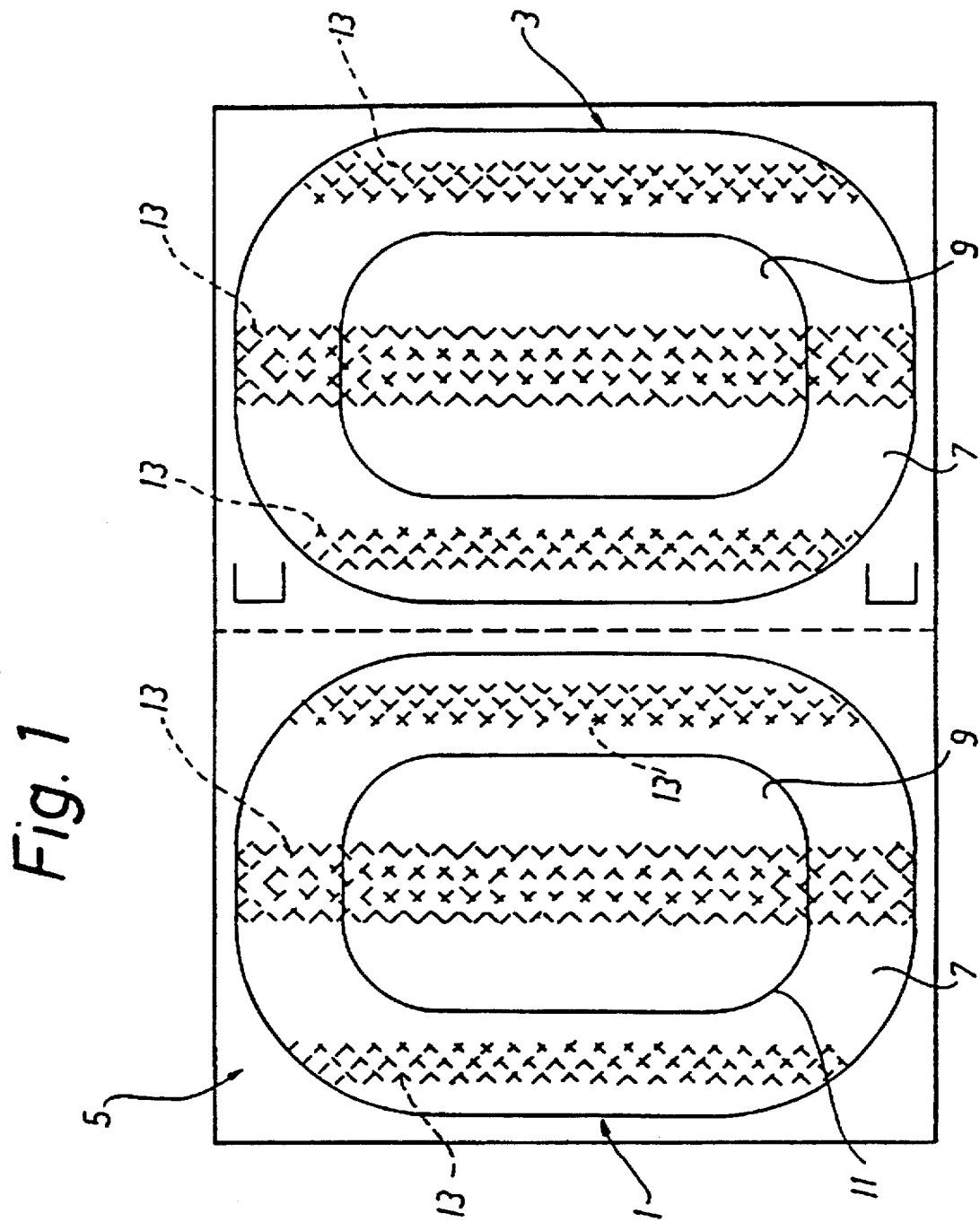
FIG. 1 is a schematic plan view of an embodiment of a device in accordance with the invention.

The device of FIG. 1 comprises two flat cover sets 1 and 3 supported on a sheet-like, specially treated rectangular carrier 5. Each set 1 and 3 includes a first ring-shaped cover 7 and a second cover 9 surrounded thereby. The form of the ring-shaped cover 7 corresponds to a conventional sealing ring (not shown) of an earmuff, on which the cover is intended to be applied. The second cover 9 completely fills out the area within the cover 7 and is at least in all essential respects separated from the latter by a stamped line 11. The covers 7 and 9 are stamped out in common from a continuous web of material. Both of the covers 7 and 9 therefore have the same construction, as is explained in more detail in connection with FIG. 3.

The covers are releasably secured to the carrier 5 specially prepared therefor, by means of streaks of glue attached to their rear sides, which glue is also intended for securing the covers to an earmuff.

During application, the covers 7 and 9 are lifted away from the carrier 5 and applied to an earmuff, the ring-shaped cover on the sealing ring of the earmuff and the second cover within the earmuff, for example on the expanded plastic insulating material which is most often located therein. As will be appreciated, the second cover has a form which is adapted to the opening into the interior of the earmuff.

Figure 2:
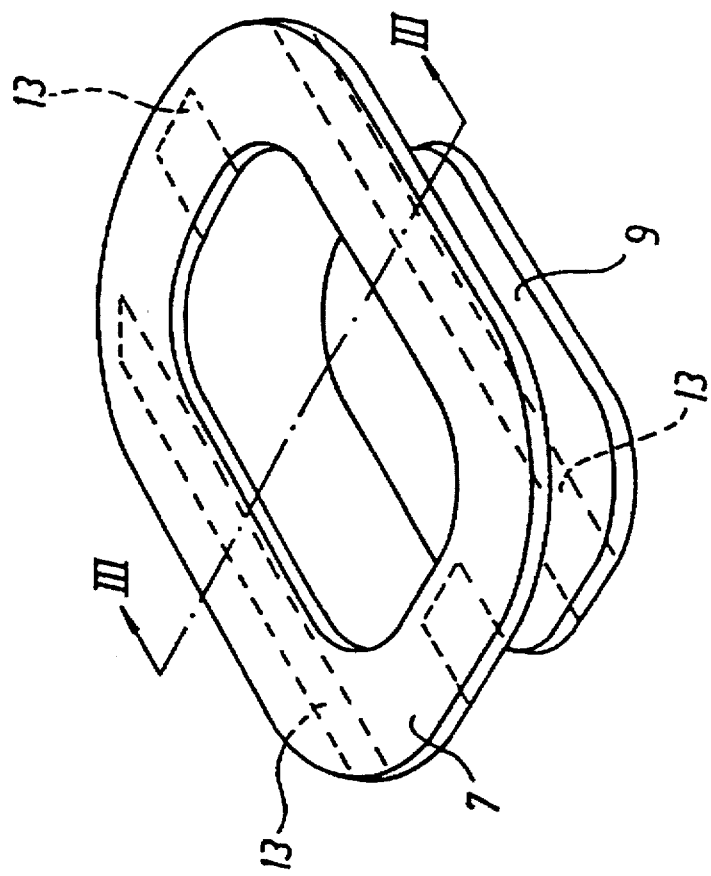
FIG. 2 is a schematic perspective view illustrating covers in accordance with the invention derived from a device in accordance with FIG. 1.

If the covers 7, 9 are completely separated from each other, they can be easily taken up and applied one at a time; compare also FIG. 2.

If the covers are in all essential respects separated from each other but can nevertheless be handled as a unit upon lifting from the carier 5, said unit can be applied to the earmuff firstly with the cover 7 over the sealing ring, after which the inner, second cover 9, while being released from the ring-shaped cover 7, is simply pushed into, and secured within, the earmuff.

Figure 3:
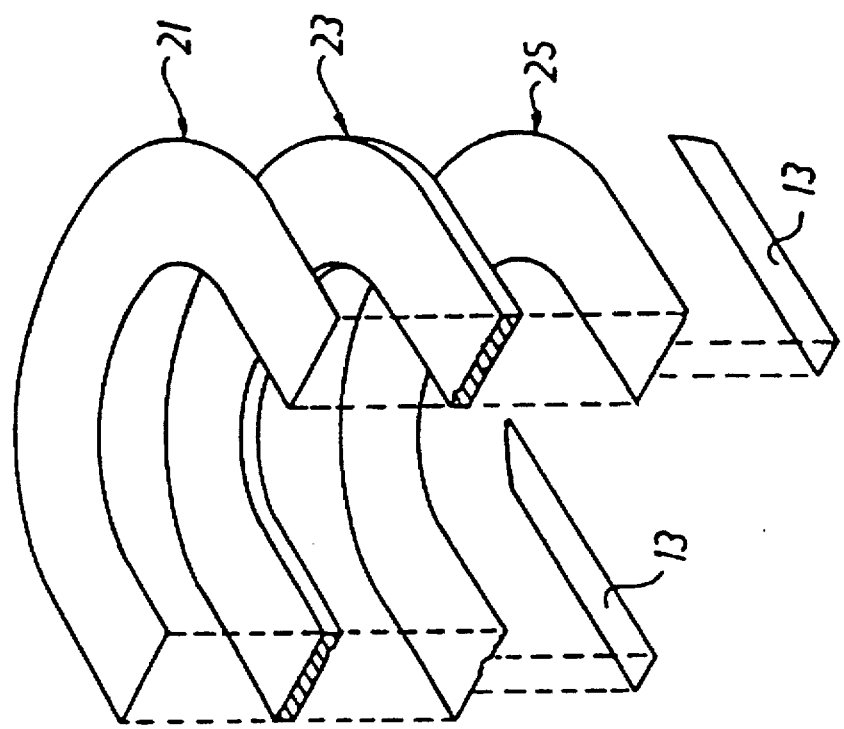
FIG. 3 is a schematic partial exploded view illustrating a section along III—III in FIG. 2.

FIG. 3 illustrates the construction of the material from which the covers 7 and 9 are prepared. The material includes an outer layer 21, an inner layer 23 and a backing layer 25, on the latter of which the streaks of glue are attached.

The surface layer 21 and the backing layer 25 are thin, impermeable layers consisting of around 25% hydrophilic cellulose fibres and around 75% staple fibres of the Bi component PP/PE type.

The inner layer 23 consists of around 15% "FSA" superabsorbent fibres which are polyacrylate based, around 65% hydrophilic cellulose fibres and around 20% staple fibres of the same type as in both of the other layers. Said superabsorbent fibres are a product developed by Allied Colloids Ltd. and Courtaulds Ltd.

The material is the form of a nonwoven web in which the staple fibres of the same type in the layers provide a cohesive and reinforcing effect.

I claim:

1. A cover for a sealing ring of an earmuff, comprising:

an inner moisture absorbing layer which includes a superabsorbent material, wherein the inner layer includes a mixture of superabsorbent fibers, hydrophilic fibers, and staple fibers, and the staple fibers are formed from polypropylene and polyethylene; and an outer layer having a high moisture permeability and being formed of a nonwoven or bonded-fiber fabric including a mixture of hydrophilic fibers and staple fibers.

2. A cover for a sealing ring of an earmuff, comprising:

an inner moisture absorbing layer which includes a superabsorbent material, wherein the inner layer includes a mixture of superabsorbent fibers, hydrophilic fibers, and staple fibers, and the staple fibers are formed from polypropylene and polyethylene; and a backing layer being adapted to be adhered to the sealing ring, the backing layer being formed of a nonwoven or bonded-fibre fabric including a mixture of hydrophilic fibers and staple fibers.

3. A cover according to claim 2, further comprising an outer layer, the outer layer having a high moisture permeability and being formed of a nonwoven or bonded-fiber fabric including a mixture of hydrophilic fibers and staple fibers, wherein the outer layer, the inner layer and the backing layer each include at least some of the same sort of fibers such that the fibers provide a cohesive and reinforcing effect.

4. A cover according to claim 3, wherein the outer layer and the backing layer each includes from around 20% to around 30% hydrophilic fibers and are otherwise of staple fibers.

5. A cover for a sealing ring of an earmuff, comprising an inner moisture absorbing layer which includes a superabsorbent material, wherein the inner layer includes from around 10% to around 20% of superabsorbent fibers and hydrophilic fibers from around 50% to around 75%, and staple fibers, wherein the staple fibers are formed from polypropylene and polyethylene; and an outer layer having a high moisture permeability and being formed of a nonwoven or bonded-fiber fabric including a mixture of hydrophilic fibers and staple fibers.

6. A cover for a sealing ring of an earmuff, comprising:

an inner moisture absorbing layer which includes a superabsorbent material, wherein the inner layer includes from around 10% to around 20% of superabsorbent fibers and hydrophilic fibers from around 50% to around 75%, and staple fibers, wherein the staple fibers are formed from polypropylene and polyethylene; and a backing layer being adapted to be adhered to the sealing ring, the backing layer being formed of a nonwoven or bonded-fibre fabric including a mixture of hydrophilic fibers and staple fibers.

7. A cover according to claim 6, further comprising an outer layer, the outer layer having a high moisture permeability and being formed of a nonwoven or bonded-fiber fabric including a mixture of hydrophilic fibers and staple fibers, wherein the outer layer, the inner layer and the backing layer each include at least some of the same sort of fibers such that the fibers provide a cohesive and reinforcing effect.

8. A device for moisture absorption in an earmuff, comprising a first sealing ring cover for an earmuff sealing ring, the first sealing ring cover including an inner moisture absorbing layer which includes a superabsorbent material, the first sealing ring cover being adapted to encompass an area on a sealing ring of an earmuff, and a supplementary second cover, the supplementary second cover being configured to correspond to the area encompassed by the first sealing ring cover, the supplementary second cover being adapted to be disposed within the earmuff inside the sealing ring and including a superabsorbent material, wherein the inner layer includes a mixture of superabsorbent fibers, hydrophilic fibers, and staple fibers, and the staple fibers are formed from polypropylene and polyethylene.

9. A device for moisture absorption in an earmuff, comprising a first sealing ring cover for an earmuff sealing ring, the first sealing ring cover including an inner moisture absorbing layer which includes a superabsorbent material including superabsorbent fibers, the first sealing ring cover being adapted to encompass an area on a sealing ring of an earmuff, and a supplementary second cover, the supplementary second cover being configured to correspond to the area encompassed by the first sealing ring cover, the supplementary second cover being adapted to be disposed within the earmuff inside the sealing ring and including a superabsorbent material, wherein the inner layer includes a mixture of superabsorbent fibers, hydrophilic fibers, and staple fibers and the staple fibers are formed from polypropylene and polyethylene.

* * * * *